United States Patent [19]

Yu et al.

[11] Patent Number: 4,904,773

[45] Date of Patent: Feb. 27, 1990

[54] PROCESS FOR EXTRACTING METHYLXANTHINES FROM AQUEOUS SOLUTIONS CONTAINING SAME

[75] Inventors: Ernest K. Yu, Brampton; Wayne R. Bellamy, Guelph; Alexander M. Sills, Thornhill, all of Canada

[73] Assignee: Allelix Inc., Mississauga, Canada

[21] Appl. No.: 23,619

[22] Filed: Mar. 9, 1987

[51] Int. Cl.$^4$ .............................. A23F 5/26; A23F 5/44
[52] U.S. Cl. ........................................ 536/103; 426/594
[58] Field of Search ........................... 536/103; 426/594

[56] References Cited

U.S. PATENT DOCUMENTS

| | | | |
|---|---|---|---|
| 3,061,444 | 10/1962 | Rogers et al. | 426/655 |
| 3,314,884 | 4/1967 | Cover | 252/10 |
| 3,465,055 | 9/1969 | Gleim et al. | 536/103 |
| 3,528,819 | 9/1970 | Hamilton et al. | 426/597 |
| 4,474,822 | 10/1984 | Sato et al. | 426/594 |
| 4,560,571 | 12/1985 | Sato et al. | 426/594 |

OTHER PUBLICATIONS

Chemical Abstracts, vol. 105, No. 15, Oct. 13, 1986, abstract 105:132445V.
Chemical Abstracts, vol. 107, No. 8, Aug. 24, 1987, abstract 107:64827K.
Process Biochemistry, May, 1979, Horikoshi.
Chemical Economy & Engineering Review, Jul./Aug. 1985, vol. 17, No. 7-8, (No. 190); Nagatoma.
J. Agric. Food Chem. 1984, vol. 32, pp. 832–836 at p. 832.

*Primary Examiner*—Ronald W. Griffin
*Attorney, Agent, or Firm*—Foley & Lardner, Schwartz, Jeffery, Schwaab, Mack, Blumenthal & Evans

[57] ABSTRACT

Methylxanthines such as caffeine are removed from aqueous solution by contact with cyclodextrin. A decaffeination process using selected cyclodextrin species is particularly disclosed.

26 Claims, No Drawings

PROCESS FOR EXTRACTING METHYLXANTHINES FROM AQUEOUS SOLUTIONS CONTAINING SAME

FIELD OF THE INVENTION

The invention described herein provides a method for treating extracts used in or as foods and beverages to reduce the content of methylxanthines e.g. caffeine.

BACKGROUND OF THE INVENTION

Methylxanthines produced naturally by certain plant species include theophylline, theobromine and, most notably, caffeine. It is generally understood that theophylline and theobromine are precursors in the in vivo production of caffeine so that the relative abundance of these three methylxanthines in the plant will depend to some extent on the metabolic efficiencies of the particular plant and to further extent on the characteristic metabolism of the particular species of plant.

Theobromine, for example is produced by *Theobroma cacao* which is a valuable source of cocoa used in the food industry, usually in the production of chocolate confections. *Cola acuminata* and other *Cola sp.*, which provide a source of cola flavorant, also produce theobromine. Sources of caffeine include *Coffea arabica, C. robustas* and other species of the coffee plant as well as the tea plant *Cammellia thea* and its relatives. Theophylline is believed to be present in each of these species but in less significant amounts than theobromine and caffeine. Extracts of these plants or, more commonly, of specific tissues of these plants e.g. coffee beans, tea leaves, etc., which are used in the preparation of foods or per se as beverages or beverage additives comprise not only the characteristic flavor factors, but also, in varying concentrations, the methylxanthines produced by the plants. For that reason, theophylline, theobromine and caffeine have been referred to as the dietary methylxanthines. The occurrence of dietary methylxanthines in foods and beverages and an assessment of their impact on health is described in The Methylxanthine Beverages and Foods, 1984, Alan R. Liss, Inc. New York.

Perhaps the most well known effect of a dietary methylxanthine is the stimulation of the central nervous system by caffeine which is experienced after consumption of coffee beverages. A similar stimulatory effect also results from consumption of foods and/or beverages prepared from theobromine-containing extracts such as cocoa-based foods and cola beverages. While theophylline is noted primarily as a muscle relaxant, it too may induce stimulation.

With the understanding that the methylxanthine effects may be undesirable, the coffee industry in particular has focused on developing processes which reduce the caffeine content of coffee extracts, at the same time retaining the pleasing taste and aroma of a beverage prepared from the treated extract.

Known processes for decaffeinating coffee focus on extracting caffeine either directly from the beans or from aqueous extracts thereof. In some processes, such as those disclosed in U.S. Pat. No. 4,547,378; EP No. 158,381, U.S. Pat. No. 4,515,695 and U.S. Pat. No. 4,505,940, caffeine is entrained in an organic solvent such as a halogenated hydrocarbon e.g. monochlorodifluoromethane or the carcinogen methylene dichloride, which is optionally further extracted to recover desired taste factors which may then be returned to the coffee extract after stripping the organic solvent. Solvent contamination of the end product, particularly with such solvents as the halogenated methanes and ethanes, is undesirable from a health viewpoint however.

An alternative process proposed in the art e.g. DE No. 3,445,502, relies on treatment with gaseous $CO_2$ under super-critical conditions to decaffeinate coffee. Pressures above 200 bar are required, making this particular process economically unattractive. Extraction rates using this type of process can be enhanced using DMSO, according to U.S. Pat. No. 4,472,442, but the problem of solvent contamination must, again, be resolved.

Literature available on processes by which theobromine and theophylline are selectively extracted from foods and beverages or additives therefor are scant but it is believed that the same problems are encountered as are present in decaffeination processes.

Accordingly, it is an object of the present invention to provide a novel process for reducing the methylxanthine content of an aqueous solution. It is a further object of the present invention to provide a process for reducing the content of dietary methylxanthines present in foods and beverages or additives therefor.

It is a further, more specific object of the present invention to provide a decaffeination process effective to reduce the caffeine content of an aqueous coffee extract.

SUMMARY OF THE PRESENT INVENTION

In accordance with the present invention, it has now been determined that methylxanthines can be removed from an aqueous solution when the solution is contacted with cyclodextrin. Complexes of the methylxanthine and cyclodextrin result from this contact and facilitate separation of the methylxanthine from the aqueous solution. The process described herein is particularly attractive since cyclodextrins are relatively inexpensive and are generally considered to be of food-grade quality.

Cyclodextrins are cyclic, non-reducing oligosaccharides composed of at least six glucose units. Cyclodextrins having six glucose units i.e. $\alpha$ cyclodextrin, seven glucose units i.e. $\beta$ cyclodextrin, and eight glucose units i.e. $\gamma$ cyclodextrin, are the most familiar cyclodextrins. In these cyclodextrins and in the corresponding polymerized species which are also useful herein most of the hydroxyl groups of the constituent glucose units are on the exterior of the ring, rendering the interior of the ring non-polar in nature. As a result of the non-polar nature of the cavity, cyclodextrins have the ability to form inclusion complexes with hydrophobic compounds.

An understanding of their chemical structure has led researches to propose many applications for cyclodextrins, some of which are summarized, for example, by Horikoshi in Process Biochemistry, May, 1979 and by Nagatomo in Chemical Economy and Engineering Review, July/August 1985, Vol. 17 No. 7-8 (No. 190). Known applications include use in stabilizing volatile substances in the chemical engineering art, complexing of active pharmaceutical agents and masking malodorant or bitter substances in foods and beverages.

U.S. Pat. No. 3,528,819 describes, for example, the use of cyclodextrins in treating extracted beverage compositions such as coffee and tea to mask "undesirable taste factors" resulting from overcooking of bitter coffee beans or tea leaves. According to the process described in the patent cyclodextrins may simply be mixed with the beverage at a concentration ranging between an amount soluble in the beverage and 1% by weight of the beverage. The patent states (column 5, line 27 et seq.) that it is an advantage that the undesirable taste factors need not be separated from the beverage because no advantage accrues from such a separation and it would even be a handicap when considering the added processing costs. Clearly, therefore, it is the patentee's intention simply to mask rather than to remove the undesirable taste factors.

The present invention, on the other hand, provides a process for removing methylxanthine, particularly a dietary methylxanthine i.e. caffeine, theobromine and theophylline, by contacting an aqueous solution thereof with cyclodextrin, separating the resultant complexes and aqueous solution and recovering a solution in which the methylxanthine content is reduced. Separation of the methylxanthine from the solution is essential to the present process, in order to provide a solution with reduced methylxanthine content.

As the terms are used herein, it is to be understood that "caffeine" refers to the chemical compound 3,7-dihydro-1,3,7-trimethyl-1H-purinedione, known synonymously in the art as coffeine, theine, methyltheobromine or guaranine depending on its natural source. For brevity herein, the more familiar term "caffeine" is used. Similarly, "theobromine" is used herein to refer to the chemical compound 3,7-dihydro-3,7-dimethyl-1H-purine-2,6-dione known synonymously as 3,7-dimethylxanthine. "Theophylline" refers to 3,7-dihydro-1,3-dimethyl-1H-purine-2,6-dione also known 1,3-dimethylxanthine and as theocin. For convenience, the chemical structures of these dietary methylxanthilnes are reproduced below:

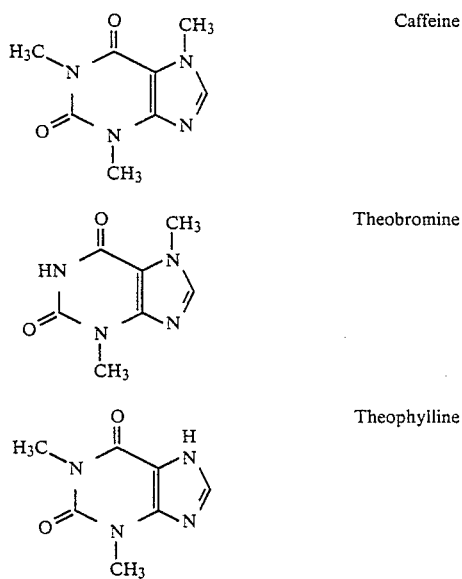

It should be understood that salts of these compounds which are able to complex with the cyclodextrins useful herein are also included, when appropriate, within the definition of the dietary methylxanthines.

Further, it is to be understood that the term "aqueous solution" is used herein to refer not to true aqueous solutions in the pure chemical sense but to water-based compositions which may or may not contain inconsequential amounts of organic solvents such as ethanol and the like and other components which result, for example, from processes by which methylxanthine-containing extracts are prepared e.g. minor amounts of oils and other components of plant tissue. The viscosity of such solution may vary e.g. from pure aqueous solutions to slurries, provided that agitation or flow of the solution to cause contact of the caffeine with cyclodextrin is possible.

The process described herein will be useful in removing methylxanthines from a variety of aqueous solutions such as those prepared from cocoa, those containing cola and those which are extracts of coffee beans and tea leaves. Further, it has been found that all cyclodextrins i.e. monomeric or polymerized, $\alpha$, $\beta$ or $\gamma$ cyclodextrin, are able to complex a methylxanthine to some extent. In accordance with the embodiments preferred herein and described below, only those cyclodextrins which show an ability to remove at least 20%, preferably at least 50% and more preferably at least 70% of the methylxanthine are used in the process.

DETAILED DESCRIPTION OF THE PREFERRED EMBODIMENTS

Selection of the cyclodextrin species most appropriate for application in the process described herein depends to a minor extent on the type of methylxanthine which predominates in the aqueous solution but is generally consistent. Those skilled in the art will appreciate that the aim is to utilize cyclodextrin species which, under the particular process conditions, will efficiently complex a desired amount of methylxanthine and which thereafter will facilitate separation of the complexed material from the treated solution.

In general, it is the solubility of the selected cyclodextrin which will dictate the type of process to be used e.g. batch, continuous or semi-continuous, and the form in which the cyclodextrin is to be used e.g. free or immobilized. It should be noted that the monomeric cyclodextrins are soluble to different extents in aqueous solution whereas, the polymerized cyclodextrins are generally insoluble in aqueous solution. Of the monomeric species, $\gamma$ cyclodextrin is soluble in aqueous solution when used in the amounts required for the process described herein. Cyclodextrin $\alpha$ is soluble to an extent similar to $\gamma$ cyclodextrin. Cyclodextrin $\beta$ is considerably less soluble, however.

The soluble monomeric cyclodextrins $\alpha$ and $\gamma$ are therefore more amenable to use in a batch process, in free form as opposed to immobilized form. In the batch process, a methylxanthine-containing aqueous solution is stirred in the present of free monomeric cyclodextrin. Stirring is not absolutely essential since the initial mixing of solution and cyclodextrin may be adequate but agitation, such as in a continuous stir tank reactor, to encourage formation of cyclodextrin/methylxanthine complexes is preferred. Complexes which form during the mixing process are preferably insoluble in the solution and are therefor able to precipitate. Precipitation can be enhanced by cooling of the solution under conditions of non-agitation or after which the treated solution may be separated from the precipitate such as by decanting, by centrifugation or by filtration.

Thus those soluble cyclodextrin species which are unable to form insoluble methylxanthine complexes are not preferred for use in the batch process described above. While complexes may form during the process, the solubility of the complexes makes separation of the complexes and the treated solution difficult. Accordingly the cyclodextrin species which are most preferred for processes which rely on precipitation such as the batch process described above will be those cyclodextrin species which are soluble to a desired extent in the solution to be treated and which are able to form insoluble complexes with a significant amount of the available methylxanthine.

In the particular case where aqueous solutions containing caffeine are to be treated by relying on precipitation, free monomeric $\gamma$ cyclodextrin is most preferably used. Of the other available monomeric species i.e. $\alpha$ and $\beta$, $\beta$ is only poorly soluble in aqueous solution. While monomeric $\alpha$ cyclodextrin is soluble to an extent in aqueous solution, experimental evidence indicated that it is unable to complex efficiently with caffeine. Moreover, even if such complexes do indeed form, they are unable to precipitate to a significant extent under static conditions, making separation difficult. A similar result will be observed in respect of theobromine and theophylline. Thus, precipitation of caffeine from solution is best accomplished using free monomeric $\gamma$ cyclodextrin.

It is obviously important that the solution being treated contain sufficient methylxanthine to elicit precipitation when complexed. As a guideline, it has been determined that for precipitation of free monomeric $\gamma$ cyclodextrin-caffeine complexes to occur, at least 1 g/L of caffeine must be present in the solution. In this particular instance, the solution was a pure caffeine/water solution and this lower limit may vary depending on the nature of the solution. Precipitates containing caffeine are likely to form at lower caffeine levels when actual plant extracts are treated.

It should be noted that polymerized cyclodextrins may be used in a similar process e.g. in a continuous stir tank reactor, despite their relative insolubility in aqueous solution. Provided that forceful agitation is maintained to the extent required to fluidize these cyclodextrins, complex formation can occur. Necessarily, the cyclodextrins must have a reasonable affinity to complex with the methylxanthine in order to remove the methylxanthine efficiently from solution. In this regard and in the particular case of the caffeine, it has been found that, polymerized $\gamma$ and polymerized $\beta$ cyclodextrin can facilitate caffeine removal in a batch process. Polymerized $\alpha$ cyclodextrin will complex caffeine to a relatively insignificant extent, although it is useful in theobromine removal. Complexed polymerized cyclodextrin can be separated from the treated solution in the manner described above e.g. filtration.

As an alternative to the agitation process described above, the cyclodextrins may be used in immobilized form rather than in free form. Immobilization relieves the need to decant or filter the treated solution to remove precipitate. Immobilization can be accomplished by linking the cyclodextrin to an inert support or by entrapping it therein or by employing a fixed bed of the cyclodextrin in a reaction vessel. Alternatively, ultrafiltration membranes may be used to contain the cyclodextrin charge yet permit contact of the solution therewith. In general, any means which permits contact between cyclodextrin and methylxanthine-containing solution in order for complexes to form and which retains the cyclodextrin in a reaction zone to eliminate the need for subsequent steps of separating complexed material from solution may be used.

For example, a packed bed reactor may be employed in which a polymerized cyclodextrin charge is retained between two supports e.g. filters, in a column. Solution containing a methylxanthine is urged into contact with the cyclodextrin in a continuous or semi-continuous manner either by percolation or by leaching and collected after adequate contact e.g. downstream of the column.

Immobilization of the cyclodextrin in the manner described above effectively eliminates concern for the solubility of the cyclodextrin complexes which are generated. While any of the monomeric or polymerized cyclodextrins may therefore be used, efficient reduction in methylxanthine content using immobilized cyclodextrins clearly demands use of only those cyclodextrins able to complex the methylxanthine efficiently. When caffeine is to be removed immobilized monomeric $\gamma$ cyclodextrin, monomeric $\beta$ cyclodextrin, polymerized $\gamma$ cyclodextrin and, most notably, polymerized $\beta$ cyclodextrin are most preferred. When theobromine is to be removed, immobilized, polymerized $\alpha$, $\beta$ or $\gamma$ cyclodextrin may be used.

Thus particularly preferred embodiments of the invention comprise the use of free monomeric $\gamma$ cyclodextrin or the use of immobilized monomeric $\gamma$ cyclodextrin, polymerized $\gamma$ cyclodextrin or polymerized $\beta$ cyclodextrin, in reducing the methylxanthine content, particularly the caffeine content, of an aqueous solution.

It is not absolutely essential to use only those cyclodextrin species which are particularly preferred herein. However, because these cyclodextrins, among others, are commercially available commodities it is clearly preferable in economic terms to avoid the cost of using additional species in the reaction. Accordingly, it is particularly preferred herein to use cyclodextrins selected from the group consisting essentially of only monomeric $\gamma$ cyclodextrin, polymerized $\gamma$ cyclodextrin and polymerized $\beta$ cyclodextrin and combinations and mixtures thereof, including monomeric $\beta$ cyclodextrin when immobilized.

It has been determined however, that species of cyclodextrin other than the preferred species are inocuous and may be present in the reaction. They will in some cases, contribute to methylxanthine removal, albeit to a relatively minor extent. Use of additional, less efficient cyclodextrin species in combination with predominant amounts of the preferred species can be economically attractive. Cyclodextrins are prepared by the action of bacterial enzymes on pregelatinized starch. The bacterial action is generally not selective and the metabolism usually results in production of all three monomeric species of cyclodextrin. With more recent techniques, enzymolysis can be controlled to favour production of a particular monomeric species e.g. monomeric $\beta$ cyclodextrin (see U.S. Pat. No. 4,317,881) or $\gamma$ cyclodextrin (see U.S. Pat. No. 4,418,144). The present invention therefore contemplates and includes the use of crude cyclodextrin mixtures in which a preferred cyclodextrin is present, predominantly preferably, in order to enhance the economic value of the process. Similarly, polymerized versions of such a crude mixture prepared using cross-linking agents such as formaldehyde, phosphorus oxychloride or epichlorohydrin for example as disclosed by Shaw et al in J. Agric. Chem, 1984, 32, 832–836 at p. 832, may be used rather than purified polymerized species provided preferably that the $\beta$ or $\gamma$ monomers predominate in the polymerizate.

Regardless of the type of cyclodextrin used in the process, repeated contact with the methylxanthine will eventually saturate the charge. The present invention therefore also includes the step of substituting a fresh charge of cyclodextrin for use in the process. In one embodiment, the spent cyclodextrin may simply be discarded and replaced with a fresh charge. Alternatively, and preferably, the spent cyclodextrin is regenerated. Regeneration may be conducted in situ at a selected process interval or in a regeneration zone isolated from the reactor. To regenerate, the methylxanthine-complexed cyclodextrin is contacted with a regenerant which is able to dissociate the methylxanthine. Examples of suitable regenerating agents include ethanol e.g. 5% ethanol, or a weak base such as 2% sodium hydroxide. In some cases, repeated washing with water may serve to release the methylxanthine. Once treated, the cyclodextrin may be reused after washing to remove solvents if necessary. Methylxanthine released by regeneration may be recovered if desired using standard chemical extraction techniques.

The methylxanthine complexing ability of the cyclodextrin used in the process will depend on several factors including the concentration and type of methylxanthine present in the solution to be treated, the species of cyclodextrin used and the amount of cyclodextrin used.

Clearly, cyclodextrin saturation by methylxanthine will be relatively fast when the solution exposed thereto has a relatively high concentration of methylxanthine. For example, treatment of diluted coffee extracts i.e. domestic coffee beverages, will require a lesser amount of cyclodextrin per unit volume of extract than will coffee extract concentrated produced on a commercial scale in coffee processing. Cyclodextrin compositions comprising only the cyclodextrins preferred herein will be the most efficient in reducing the caffeine content. Greater relative amounts of cyclodextrin will be required when less efficient species of cyclodextrin are included.

It is believed that persons skilled in this art will readily comprehend the need for specific experimental trials in order to tailor the present process particularly to a desired decaffeination or other related process and will be able to determine processing parameters such as solution flow rates, amounts and type of cyclodextrins to be used, etc. The examples which follow to illustrate embodiments of the invention will be of particular assistance in this regard.

The monomeric $\alpha$, $\beta$ and $\gamma$ cyclodextrins used in the following experiments were obtained from American Maize, Hammond, Indiana U.S.A. Caffeine and theorbromine were purchased from Sigma Chemical Company, St. Louis, Mo., U.S.A.

Polymerized cyclodextrins were prepared from the purchased monomeric cyclodextrins using the process described by Shaw et al., Journal of Agricultural Food Chemistry, 32, 832–836, 1984. Briefly stated, the process comprises treating a mixture of monomeric cyclodextrin and water with sodium hydroxide and then with $NaBH_4$ followed by reaction with epichlorohydrin. The product is heated to 50° C., washed with acetone and then ethanol. It is to be understood, however, that a variety of other polymerizing processes and cross-linking agents such as formaldehyde, phosphorous oxychloride or the like may be used.

The samples tested in the following examples included:

Aqueous caffeine solution: varying amounts of caffeine were dissolved in distilled water and used per se.

Aqueous theobrimine solution: 0.1 mg/mL water.

Concentrated coffee extract: prepared by placing 1 bag of Melitta drip coffee crystals in 60 mL of boiling water, let stand for 30 minutes with occasional stirring and then filtering through domestic coffee filter paper at about 50° C. and collecting the filtrate.

Concentrated tea extract: prepared by submerging one domestic tea bag in 40 mL boiling water, mixing for 30 minutes and collecting the supernatant.

Cocoa solution: prepared by dissolving 7.0 g (one spoonful) of pure cocoa Hershey in 200 mL boiling water.

Instant coffee drink: prepared by dissolving 3.0 g (one spoonful of Nescafe instant coffee in 200 mL of boiling water.

Cola drink: sample of Diet Coke per se.

The caffeine content in the control and test samples was measured using UV absorbance, GC and/or HPLC. Relative caffeine concentrations are best determined using either UV-absorbance or GC whereas more precise data is generated using the HPLC assay. Purified caffeine absorbs maximally in the UV spectrum at 275 nm. Optical absorbance, determined herein using a Beckman DU-40 Spectrophotometer, is linearly proportional to caffeine concentration ranging from 5–50 $\mu$g/mL. Decaffeination of aqueous solutions of pure caffeine can be readily monitored by UV absorbance.

GC analysis was performed using a 30 m Durabond DB5 capillary column (J&W Scientific Inc.) under the following parameters: oven temp=250° C., injection temp=275° C., FID temp=300° C.; heliumas carrier gas; operating pressure=10 psig and use of flame ionization (FID) as detector.

HPLC analysis was performed using Nova-Pak™, 3.9 mm×15 cm, mobile phase $CH_3OH$: P1C reagent B8, 27:73, flow rate of 1.0 mL/min and UV detection at 254 nm.

EXAMPLE 1

Aqueous solutions of caffeine at various concentrations were subjected to batch reaction with various amounts of monomeric cyclodextrins $\gamma$ (shown in Table 1), $\alpha$ and $\beta$ (shown in Table 2). Cyclodextrin and caffeine solution were incubated with shaking at 50° C. for from 30 minutes to 18 hours. The mixtures were then incubated at 4° C. for 30–90 minutes. Precipitates were removed either by centrifugation or filtration. Supernatant fluids or filtrates were collected and assayed for residual caffeine content.

The results of the decaffeination processes using free monomeric $\gamma$-cyclodextrin are shown below in Table 1.

TABLE 1

Caffeine at varying concentrations treated with free monomeric $\gamma$-cyclodextrin

| $\gamma$-CD concentration (g/mL) | Original caffeine concentration (mg/mL) | Caffeine removed (mg/mL) | % caffeine removal |
|---|---|---|---|
| 0.13 | 0.5 | 0.0 | 0.0 |
|  | 1.0 | 0.0 | 0.0 |
|  | 2.0 | 0.2 | 10.0 |
|  | 3.0 | 1.2 | 40.0 |
|  | 4.0 | 2.2 | 55.0 |
|  | 5.0 | 4.0 | 80.0 |
|  | 7.5 | 6.6 | 88.0 |
|  | 10.0 | 7.8 | 78.0 |
|  | 15.0 | 13.5 | 90.0 |
|  | 20.0 | 16.5 | 82.5 |

TABLE 1-continued

Caffeine at varying concentrations treated with free monomeric γ-cyclodextrin

| γ-CD concentration (g/mL) | Original caffeine concentration (mg/mL) | Caffeine removed (mg/mL) | % caffeine removal |
|---|---|---|---|
| 0.065 | 2.0 | 0.0 | 0.0 |
| | 4.0 | 1.2 | 30.0 |
| | 6.0 | 2.8 | 46.7 |
| | 8.0 | 4.2 | 52.5 |
| | 10.0 | 6.2 | 62.0 |
| | 15.0 | 11.6 | 77.3 |
| | 20.0 | 15.2 | 76.0 |
| 0.013 | 2.0 | 0.0 | 0.0 |
| | 4.0 | 0.54 | 13.5 |
| | 6.0 | 2.30 | 38.3 |
| | 8.0 | 3.19 | 39.9 |
| | 10.0 | 4.75 | 47.5 |
| | 15.0 | 7.50 | 50.0 |
| | 20.0 | 11.75 | 58.8 |

It will be noted from Table 1 that the ability of free monomeric γ-cyclodextrin to decaffeinate the caffeine solution increases as the amount of γ-CD is increased. Moreover, it will be noted that the ability of a given amount of γ-CD to decaffeinate increases with the amount of caffeine present in the test sample. A saturation point is reached, indicating that the sample should be treated again with fresh γ-CD if further decaffeination is desired or that a greater amount of γ-CD should be used to treat those samples having higher caffeine concentrations. It should be emphasized that the "% caffeine removal" values are approximate i.e. were assessed for comparative purposes only, and that actual caffeine removal values are generally higher than indicated when measured by the more sensitive HPLC assay.

The data appearing below in Table 2 demonstrate the inefficiency with which free monomeric α and β cyclodextrins decaffeinate the solution. Superior decaffeination efficiency of free monomeric γ-cyclodextrin is evident with little or no decaffeination occurring at lower caffeine concentrations when free monomeric α and β cyclodextrins are employed in the process.

TABLE 2

Caffeine at varying concentrations treated with free monomeric α- and β-cyclodextrins

| CD Concentration (g/mL) | Original caffeine concentration (mg/mL) | Caffeine removed (mg/mL) | % caffeine removal |
|---|---|---|---|
| α-CD, 0.10 g/mL | 0.5 | 0.0 | 0.0 |
| | 1.0 | 0.0 | 0.0 |
| | 2.0 | 0.0 | 0.0 |
| | 3.0 | 0.0 | 0.0 |
| | 4.0 | 0.0 | 0.0 |
| | 5.0 | 0.5 | 10.0 |
| | 10.0 | 3.4 | 34.0 |
| | 20.0 | 4.7 | 23.5 |
| β-CD, 0.018 g/mL | 0.5 | 0.0 | 0.0 |
| | 1.0 | 0.0 | 0.0 |
| | 2.0 | 0.0 | 0.0 |
| | 3.0 | 0.0 | 0.0 |
| | 4.0 | 0.0 | 0.0 |
| | 5.0 | 0.0 | 0.0 |
| | 10.0 | 1.1 | 11.0 |
| | 20.0 | 1.8 | 9.0 |

EXAMPLE 2 the decaffeination efficiencies of the polymeric cyclodextrins were analyzed as described in Example 1.

Results of the decaffeination processing using varying amounts of free polymeric γ-cyclodextrin appear in Table 3 below.

TABLE 3

Caffeine at varying concentrations treated with free polymerized γ-CD

| Polymerized γ-CD concentration (g/mL) | Original caffeine concentration (mg/mL) | Caffeine removed (mg/mL) | % caffeine removal |
|---|---|---|---|
| 0.20 | 0.5 | 0.39 | 78.0 |
| | 1.0 | 0.74 | 74.0 |
| | 2.0 | 1.48 | 74.0 |
| | 3.0 | 2.17 | 72.3 |
| | 4.0 | 2.90 | 72.5 |
| | 5.0 | 3.62 | 72.4 |
| | 7.5 | 5.55 | 74.0 |
| | 10.0 | 7.50 | 75.0 |
| | 15.0 | 13.30 | 88.7 |
| | 20.0 | 17.30 | 86.5 |
| 0.10 | 2.0 | 1.20 | 60.0 |
| | 5.0 | 3.07 | 61.4 |
| | 7.5 | 4.50 | 60.0 |
| | 10.0 | 6.50 | 65.0 |
| | 15.0 | 13.00 | 86.7 |
| | 20.0 | 15.80 | 79.0 |
| 0.065 | 2.0 | 1.30 | 65.0 |
| | 4.0 | 2.78 | 69.5 |
| | 6.0 | 4.53 | 75.5 |
| | 8.0 | 5.10 | 63.8 |
| | 10.0 | 6.20 | 62.0 |
| | 15.0 | 9.56 | 63.7 |
| | 20.0 | 9.00 | 45.0 |
| 0.013 | 2.0 | 0.42 | 21.0 |
| | 4.0 | 1.80 | 45.0 |
| | 6.0 | 2.77 | 46.2 |
| | 8.0 | 3.56 | 44.5 |
| | 10.0 | 3.70 | 37.0 |
| | 15.0 | 4.31 | 28.7 |
| | 20.0 | 4.00 | 20.0 |

TABLE 4

Caffeine at varying concentrations treated with free polymerized β-CD

| Polymerized β-CD concentration | Original caffeine concentration (mg/mL) | Caffeine removed (mg/mL) | % caffeine removal |
|---|---|---|---|
| 0.20 | 0.5 | 0.40 | 80.0 |
| | 1.0 | 0.78 | 78.0 |
| | 2.0 | 1.55 | 77.5 |
| | 3.0 | 2.32 | 77.3 |
| | 4.0 | 3.10 | 77.8 |
| | 5.0 | 3.87 | 77.4 |
| | 7.5 | 6.60 | 88.0 |
| | 10.0 | 8.00 | 80.0 |
| | 15.0 | 13.50 | 90.0 |
| | 20.0 | 18.50 | 92.5 |
| 0.10 | 2.0 | 1.55 | 77.5 |
| | 5.0 | 4.00 | 80.0 |
| | 7.5 | 5.90 | 78.7 |
| | 10.0 | 7.60 | 76.0 |
| | 15.0 | 11.40 | 76.0 |
| | 20.0 | 17.30 | 86.6 |
| 0.055 | 2.0 | 1.55 | 77.5 |
| | 4.0 | 3.20 | 80.0 |
| | 6.0 | 4.92 | 82.0 |
| | 10.0 | 8.62 | 86.2 |
| | 15.0 | 12.00 | 80.0 |
| | 20.0 | 13.25 | 66.3 |
| 0.011 | 2.0 | 0.50 | 40.0 |
| | 4.0 | 1.73 | 43.3 |
| | 6.0 | 3.30 | 55.0 |
| | 10.0 | 5.00 | 50.0 |
| | 15.0 | 8.06 | 53.7 |
| | 20.0 | 6.25 | 31.3 |

The ability of free polymeric cyclodextrins β and γ to decaffeinate the test solutions is confirmed in Tables 3 and 4. Both cyclodextrins are able to complex caffeine present in relatively low concentrations and in relatively high concentrations. As with free monomeric γ-cyclodextrins, there is a trend indicating that as the amount of the cyclodextrin is increased, the ability to complex a greater amount of caffeine increases.

Free polymeric α-cyclodextrin, on the other hand exhibits a relatively poor ability to complex caffeine, by comparison with the polymeric β and γ cyclodextrins and with monomeric γ cyclodextrin. Results of decaffeination using polymeric α-cyclodextrin appear in Table 5 below.

TABLE 5

Caffeine at varying concentrations treated with polymerized α-CD

| Polymerized α-CD concentration (g/mL) | Original caffeine concentration (mg/mL) | Caffeine removed (mg/mL) | % caffeine removal |
|---|---|---|---|
| 0.010 | 2.0 | 0.15 | 7.5 |
|  | 4.0 | 0.45 | 11.2 |
|  | 6.0 | 0.67 | 11.2 |
|  | 8.0 | 1.00 | 12.5 |
|  | 10.0 | 1.00 | 10.0 |
|  | 15.0 | 1.50 | 10.0 |
|  | 20.0 | 1.25 | 6.3 |
| 0.050 | 2.0 | 0.27 | 13.5 |
|  | 10.0 | 3.00 | 30.0 |
| 0.100 | 2.0 | 0.35 | 17.5 |
|  | 10.0 | 2.12 | 21.2 |
| 0.200 | 2.0 | 0.42 | 21.0 |
|  | 10.0 | 2.05 | 20.5 |

Equivalent amounts of polymeric β and γ cyclodextrin can facilitate the removal of between three and four times more caffeine than can polymeric α cyclodextrin (compare the % removal values when a 0.20 g/L solution of each cyclodextrin is used to treat a 10 mg/mL caffeine solution). While polymeric α-cyclodextrin is unable to decaffeinate to a significant and desirable extent, per se, its presence in a cyclodextrin composition comprising preferred cyclodextrin species, is unlikely to be deleterious, as exemplified in Table 6 below.

TABLE 6

Caffeine - initial concentration at 5 mg/mL

| Cyclodextrins used | Cyclodextrin conc'n (mg/mL) | Caffeine removed (mg/mL) | % caffeine removal |
|---|---|---|---|
| I. Free, monomeric CD's: | | | |
| γ-CD | 50 | 1.2 | 24.0 |
| β-CD | 10 | 0.2 | 4.0 |
| α-CD | 20 | 0.1 | 2.0 |
| γ + β + α | 50-10-20 | 1.5 | 30.0 |
| γ + β | 50-10 | 1.2 | 24.0 |
| γ + α | 50-20 | 1.3 | 26.0 |
| II. Polymerized CD's: | | | |
| γ | 50 | 3.4 | 68.0 |
| β | 20 | 2.4 | 48.0 |
| α | 20 | 0.6 | 12.0 |
| γ + β + α | 50-20-20 | 4.2 | 84.0 |
| γ + β | 50-20 | 4.0 | 80.0 |
| γ + α | 50-20 | 3.4 | 68.0 |

The ability of monomeric γ cyclodextrin per se to decaffeinate the solution is not hindered when monomeric α and β cyclodextrins are present. Similarly, the presence of polymerized α cyclodextrin does not destroy the superior effects of polymerized β and γ cyclodextrins.

EXAMPLE 3

The relative abilities of the preferred cyclodextrin species in facilitating caffeine removal from an aqueous caffeine solution was tested as described in Example 1 and analyzed by UV absorbance, GC and HPLC. The results appear below in Table 7.

TABLE 7

Caffeine removal by free monomeric γ-CD (0.13 g/mL) and polymerized γ-CD (0.2 g/mL) and β-CD's (0.2 g/mL). Confirming data by UV absorbance, GC and HPLC analyses.

| Caffeine Concen. (mg/mL) | Cyclodextrin Used | UV(275 nm) | | GC | | HPLC | |
|---|---|---|---|---|---|---|---|
| | | Caffeine Present (mg/mL) | % removal | Caffeine Present (mg/mL) | % removal | Caffeine Present (mg/mL) | % removal |
| 1.0 | γ-CD | 1.00 | 0.0 | — | — | 1.00 | 0.0 |
|  | polymerized γ-CD | 0.28 | 72.5 | — | — | 0.00 | 100.0 |
|  | polymerized β-CD | 0.25 | 72.5 | — | — | — | — |
| 2.0 | γ-CD | 1.80 | 10.0 | — | — | — | — |
|  | polymerized γ-CD | 0.62 | 69.8 | 0.20 | 90.0 | 0.19 | 90.5 |
|  | polymerized β-CD | 0.39 | 81.5 | 0.00 | 100.0 | 0.05 | 97.5 |
| 10.0 | γ-CD | 2.20 | 78.0 | — | — | 4.50 | 55.0 |
|  | polymerized γ-CD | 2.50 | 75.0 | — | — | 4.55 | 54.5 |
|  | polymerized β-CD | 2.00 | 80.0 | — | — | 1.60 | 84.0 |

It will be noted that both preferred polymeric cyclodextrins function well over a range of caffeine concentrations, each exhibiting an ability to remove caffeine completely from the test solution at one or another caffeine concentration depending upon the analytical method employed. Monomeric γ-cyclodextrin is most suited, according to the data in Table 7, to complexing caffeine present in concentrations higher than 1.0 mg caffeine per mL water when present at 0.13 g/mL in the exemplified process. It has been determined however, that in processes conducted on actual coffee extracts as opposed to pure test solutions of caffeine, the cyclodextrins will remove caffeine present in concentrations lower than 1.0 mg/mL.

EXAMPLE 4

In this example, the ability of polymeric β-cyclodextrin to facilitate caffeine removal using a column process i.e. using immobilized polymeric β-cyclodextrin was determined. Five grams of polymerized β-CD were slurry packed in a 28×133 mm Bio Rad Econo column, equilibrated with water and then 5 mL of a 1 mg caffeine/mL water rest solution were allowed to pass through the column by gravity. The column packings were then washed with 5 mL volumes of water and and each washing solution was collected separately and analyzed for caffeine content. Ninety percent of the caffeine in the test sample was removed by single passage through the column.

While any aqueous solution containing caffeine may be decaffeinated using the preferred cyclodextrin species, the process is amenable primarily to decaffeination of domestic beverages or aqueous concentrates from which these beverages are prepared, such as cola beverages, coffee, tea and food and beverages comprising cocoa such as chocolate. Decaffeination of these beverages is exemplified in the following Tables 8, 9 and 10. Table 8 below provides the results of a batch process conducted on coffee and tea extracts with monomeric γ-cyclodextrin.

TABLE 8

Concentrated coffee and tea extract treated with free monomeric γ-cyclodextrin (0.065 g/mL)

|  | Caffeine present (GC analysis, mg/mL) | % caffeine removal |
|---|---|---|
| Coffee extract | 1.92 | — |
| Coffee extract + γ-CD | 0.77 | 59.9 |
| Tea extract | 1.08 | — |
| Tea extract + γ-CD | 0.20 | 81.5 |

Decaffeination rates are significant with respect to both coffee and tea extracts. By interpolation using data presented hereinabove, decaffeination can be expected to improve when the cyclodextrin is present in greater quantities.

A similar significant decaffeination result is seen in Table 9 below which illustrates the effect of free polymerized β- and γ-cyclodextrins on the coffee and tea extracts.

TABLE 9

Concentrated coffee and tea extracts treated with polymerized β- and γ-CD (0.1 g/mL) in a batch process

|  | Caffeine present (HPLC, mg/mL) | % caffeine removal |
|---|---|---|
| Coffee extract | 1.30 | — |
| Coffee extract + polymerized γ-CD | 0.37 | 71.5% |
| Coffee extract + polymerized β-CD | 0.30 | 77.0% |
| Tea extract | 1.12 | — |
| Tea extract + polymerized γ-CD | 0.40 | 64.3 |
| Tea extract + polymerized β-CD | 0.09 | 92.0 |

Table 10 illustrates the relative abilities of the various preferred cyclodextrins in decaffeinating other domestic beverages.

TABLE 10

Decaffeination of cocoa, instant coffee, tea extracts and diet cola drinks by cyclodextrins.

|  | Caffeine present (HPLC, mg/mL) | % caffeine removal |
|---|---|---|
| Cocoa | 0.07* | — |
| Cocoa + free monomeric γ-CD (0.13 g/mL) | 0.04 | 42.9 |
| Cocoa + polymerized α-CD (0.20 g/mL) | 0.07 | 0.0 |
| Cocoa + polymerized β-CD (0.20 g/mL) | 0.00 | 100.0 |
| Cocoa + polymerized γ-CD (0.20 g/mL) | 0.00 | 100.00 |
| Instant coffee | 0.72 | — |
| Instant coffee + free monomeric γ-CD | 0.38 | 47.2 |
| Instant coffee + polymerized α-CD | 0.64 | 11.1 |
| Instant coffee + polymerized β-CD | 0.00 | 100.0 |
| Instant coffee + polymerized γ-CD | 0.14 | 80.6 |
| Tea extract | 1.22 | — |
| Tea extract + free monomeric γ-CD | — | — |
| Tea extract + polymerized α-CD | 1.06 | 13.1 |
| Tea extract + polymerized β-CD | 0.37 | 69.7 |
| Tea extract + polymerized γ-CD | 0.94 | 23.0 |
| Diet cola | 0.20 | |
| Diet cola + free monomeric γ-CD | 0.08 | 60.0 |
| Diet cola + polymerized α-CD | 0.08 | 60.0 |
| Diet cola + polymerized β-CD | 0.00 | 100.0 |
| Diet cola + polymerized γ-CD | 0.00 | 100.0 |

*GC analysis reveals 0.9 mg/mL caffeine and complete removal by polymerized β cyclodextrin.

Certain of the data in Table 10 are particularly significant. For example, polymeric α-cyclodextrin is unable to decaffeinate any of the solutions to an appreciable extent. Its somewhat significant effect on diet cola is surpassed by far superior decaffeination with monomeric γ and polymeric β and γ cyclodextrins. Of the three cyclodextrin species preferred herein, the polymeric species are the most outstanding in many of the applications proposed herein.

The polymerized cyclodextrins are for example, useful also in removing theobromine from a solution. Table 11 below provides data generated using free polymeric cyclodextrins and free monomeric γ cyclodextrin.

TABLE 11

| Sample | Cyclodextrin used | Cyclodextrin concentration (mg/mL) | % Theobromine removed |
|---|---|---|---|
| Theobromine (0.1 mg/mL) | — | — | — |
|  | γ-CD | 0.13 | 14.0 |
|  | polymerized α-CD | 0.10 | 63.8 |
|  | polymerized β-CD | 0.11 | 60.6 |
|  | polymerized γ-CD | 1.13 | 93.8 |
| Cocoa (0.48 mg/mL) | — | — | — |
|  | γ-CD | 0.13 | 14.6 |
|  | polymerized α-CD | 0.10 | 18.3 |
|  | polymerized β-CD | 0.11 | 68.6 |
|  | polymerized γ-CD | 0.13 | 69.4 |

It is suggested that the selected cyclodextrins be used particularly in the industrial scale decaffeination of coffee extracts in order to provide decaffeinated coffee crystals for commercial sale, after the coffee beans are processed in an otherwise conventional manner. Other specific applications will be apparent from an understanding of the invention as it has been described herein.

For example, the process may be conducted on a domestic scale by the end user. Brewing of coffee in the household may be accomplished in the manner described herein by using a conventional filter coated with the preferred cyclodextrins or which entraps those cyclodextrins within. The coffee grounds and cyclodextrins are trapped by the filter and decaffeinated coffee is collected as usual. Alternatively, individual cups of coffee may be treated by stirring with a disposable implement coated with cyclodextrin.

We claim:

1. A process for treating an aqueous solution containing a methylxanthine, which comprises the steps of
    (1) contacting said aqueous solution with an effective amount of cyclodextrin to produce cyclodextrin-methylxanthine complexes and a treated solution, said treated solution comprising less than 80% of the methylxanthine in said aqueous solution; and
    (2) recovering said treated solution.

2. The process according to claim 1 wherein the methylxanthine is a dietary methylxanthine.

3. The process according to claim 2 wherein the dietary methylxanthine is caffeine.

4. The process according to claim 3 wherein the cyclodextrin is immobilized.

5. The process according to claim 4 wherein the cyclodextrin is selected from monomeric $\beta$ cyclodextrin, monomeric $\gamma$ cyclodextrin, polymerized $\beta$ cyclodextrin and polymerized $\gamma$ cyclodextrin.

6. The process according to claim 4 wherein the cyclodextrin is selected from monomeric and polymerized $\beta$ cyclodextrin.

7. The process according to claim 3 wherein the cyclodextrin is free.

8. The process according to claim 7 wherein the cyclodextrin is selected from monomeric $\gamma$ cyclodextrin, polymerized $\beta$ cyclodextrin and polymerized $\gamma$ cyclodextrin.

9. The process according to claim 7 wherein the cyclodextrin is monomeric $\gamma$ cyclodextrin.

10. The process according to claim 2 wherein the dietary methylxanthine is theobromine and the cyclodextrin is in free or immobilized form.

11. The process according to claim 10 wherein the cyclodextrin is a polymerized cyclodextrin in free form.

12. The process according to claim 1 wherein the cyclodextrin is polymerized $\gamma$ cyclodextrin.

13. The process according to claim 1 wherein the cyclodextrin is regenerated from the methylxanthine-cyclodextrin complexes formed during said contact.

14. The process according to claim 13 wherein the methylxanthine released by regeneration of the said complexes is recovered.

15. A process according to claim 1, wherein (A) said aqueous solution is an aqueous coffee extract and (B) said methylxanthine is caffeine.

16. The process according to claim 15 wherein the aqueous coffee extract is mixed with free monomeric $\gamma$ cyclodextrin, the extract is separated from precipitated caffeine-cyclodextrin complexes and then the extract so treated is recovered.

17. The process according to claim 16 wherein the extract is exposed to a reaction zone containing immobilized cyclodextrin for a period of time sufficient for caffeine to complex with the cyclodextrin and the extract is then recovered.

18. The process according to claim 16 wherein the cyclodextrin is selected from monomeric $\gamma$ cyclodextrin, monomeric $\beta$ cyclodextrin, polymerized $\gamma$ cyclodextrin and polymerized $\beta$ cyclodextrin.

19. The process according to claim 18 wherein the cyclodextrin is polymerized $\beta$ cyclodextrin.

20. A process according to claim 1, wherein said methylxanthine is theobromine.

21. The process according to claim 20 wherein the cyclodextrin is in free form.

22. The process according to claim 1 wherein the aqueous solution containing methylxanthine is selected from an aqueous coffee extract or concentrate thereof, an aqueous tea extract or concentrate thereof, a cola extract or concentrate thereof and an aqueous solution containing cocoa.

23. A process according to claim 1, wherein said treated solution comprises less than 50% of said methylxanthine in said aqueous solution.

24. A process according to claim 1, wherein said treated solution comprises less than 30% of said methylxanthine in said aqueous solution.

25. A process according to claim 1, wherein said cyclodextrin comprises a mixture comprised of one or more of the group consisting of monomeric $\gamma$-cyclodextrin, polymerized $\gamma$-cyclodextrin, polymerized $\beta$-cyclodextrin, immobilized $\beta$-cyclodextrin, and another cyclodextrin.

26. A process according to claim 1, wherein step 1 is carried out at a temperature of about 50° C.

* * * * *